United States Patent [19]
Dorn et al.

[11] Patent Number: 5,523,466
[45] Date of Patent: Jun. 4, 1996

[54] DIACYLPEROXIDE ESTERS

[75] Inventors: Maximilian Dorn, Pullach; Eberhard Hägel, Icking; Klaus Kohlhammer, Marktl, all of Germany

[73] Assignees: Peroxid Chemie GmbH; Wacker-Chemie GmbH

[21] Appl. No.: 448,380

[22] PCT Filed: Jan. 28, 1994

[86] PCT No.: PCT/EP94/00237

§ 371 Date: Jun. 7, 1995

§ 102(e) Date: Jun. 7, 1995

[87] PCT Pub. No.: WO94/17037

PCT Pub. Date: Aug. 4, 1994

[30] Foreign Application Priority Data

Jan. 29, 1993 [DE] Germany .......................... 43 02 523.4

[51] Int. Cl.[6] .................................................. C07C 69/347
[52] U.S. Cl. .......................... 560/201; 526/322; 560/95; 560/118; 560/127; 568/566
[58] Field of Search ........................ 560/95, 118, 127, 560/201; 568/566; 526/322

[56] References Cited

U.S. PATENT DOCUMENTS

| | | | |
|---|---|---|---|
| 3,956,269 | 5/1976 | Sheppard et al. | 260/192 |
| 4,151,106 | 4/1979 | Meenen | 252/186 |
| 4,155,937 | 5/1979 | Haas | 260/599 |
| 5,304,609 | 4/1994 | Kohlhammer et al. | 525/309 |

*Primary Examiner*—José G. Dees
*Assistant Examiner*—Barbara S. Frazier
*Attorney, Agent, or Firm*—Felfe & Lynch

[57] ABSTRACT

Disclosed is a diacylperoxide vinyl ester of the general formula I

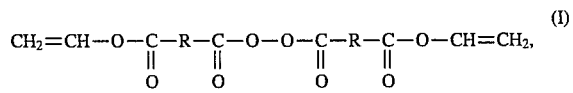

in which R is an alkylene residue which can be straight-chained, branched or cyclic and which can contain 2 to 10 C atoms or R is an aryl residue, suitable for copolymerization with olefinic unsaturated monomers under conditions in which they do not yet radically decompose.

14 Claims, No Drawings

DIACYLPEROXIDE ESTERS

BACKGROUND OF THE INVENTION

The invention concerns new diacylperoxide esters, the production and use thereof.

Diacylperoxides of the general formula $$R-CO-O-O-CO-R$$

represent versatile polymerization catalysts. The catalytic properties are due to the ready formation of radicals that can trigger a polymerization. They are usually admixed with the monomers to be polymerized and develop their catalytic activity under the applied polymerization conditions. Since polymerizations are often also carried out in several steps during which intermediate products are formed that are subjected to further polymerization reactions, there is a need for polymerization catalysts which are themselves capable of polymerization and are able to copolymerize with other monomers under conditions which do not yet cause a radical decomposition of their peroxidic structures, but when they are incorporated in the polymer they form radicals under other conditions and thus facilitate a further polymerization.

Compounds which are suitable for radical formation which contain more than one group in the molecule capable of polymerization are of particular interest in this connection. The object of the invention is to provide such compounds capable of radical formation and which contain more than one olefinic double bond.

THE INVENTION

This above stated object is achieved according to the invention by diacylperoxide vinyl esters of the general formula I

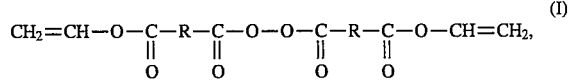

in which R denotes an alkylene residue which can be straight-chained, branched or cyclic and can contain 2 to 10 C atoms or denotes an aryl residue.

The compounds according to the invention have a good stability with half-times of about 10 hours at temperatures between about 45° and 54° C. and can therefore be used as comonomers for copolymerizations at temperatures of up to about 50° C. without thereby substantially reducing the active oxygen (AO) content that is introduced into the copolymerisate by the compounds according to the invention. At higher temperatures, in particular above about 70° C., the compounds according to the invention develop initiator activities and are particularly suitable as polymerization initiators at temperatures of 80° C. and above. Phenolic compounds such as e.g. tert-butyl pyrocatechol are particularly suitable as stabilizer additives.

The production of the compounds according to the invention is carried out according to the process of the invention starting with the appropriate dicarboxylic acid semiesters. According to a first embodiment of the process according to the invention for the production of diacylperoxide vinyl esters of the general formula I, a monovinyl dicarboxylic acid of formula II

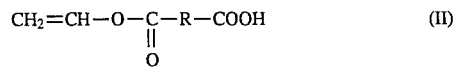

in which R has the meaning stated for formula I, is reacted with at least equimolar amounts of dicyclohexylcarbodiimide and $H_2O_2$ and catalytic amounts of an aromatic amine while cooling in an apolar aprotic solvent.

Toluene is preferred as the apolar aprotic solvent; other aliphatic and aromatic hydrocarbons as well as halogenated hydrocarbons also come into consideration. Dimethylaminopyridine is preferred as a catalytically active aromatic amine. Among the compounds of formula II those are preferred in which R represents an alkylene residue with 4 or 6 C atoms, a cyclohexylene residue or a phenyl residue which is substituted if desired. Substituents on the phenyl residue may be straight-chained or branched alkyl residues with 1 to 4 C atoms. Monovinyladipic acid is particularly preferred as the starting material.

The production of compounds of the general formula I can be carried out according to the process of DE-AS 1 222 4 93, either by transesterification with a vinyl ester of a lower aliphatic carboxylic acid or by reaction with acetylene in the presence of a catalyst.

According to a further embodiment of the process according to the invention for the production of compounds of the general formula I, a monovinyldicarboxylic acid chloride of formula III

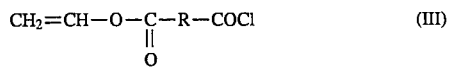

in which R has the meaning stated for formula I is reacted with an alkaline aqueous $H_2O_2$ solution at a temperature of $-10°$ to $+10°$ C. In this embodiment of the process of the invention the $H_2O_2$ is preferably used in an excess in relation to the acid chloride. A molar difference of 20 to 40% has proven to be particularly expedient.

With reference to the preferably used compounds of formula III, the same applies as stated for the first embodiment of the process according to the invention. Compounds in which R denotes alkylene with 4 or 6 carbon atoms, cyclohexylene or phenylene are particularly preferred. The production of the starting compounds of the general formula III can be carried out by reacting a monovinyl ester of the dicarboxylic acid with phosphorus trichloride.

The diacylperoxides of the general formula I according to the invention are particularly suitable for copolymerization with other olefinic unsaturated monomers, in particular with those from the group vinyl acetate, ethylene, styrene, vinyl chloride, vinylidene chloride, methacrylate and methylacrylate. In this case it is expedient to carry out the copolymerization at temperatures of maximally 50° C., preferably 30° to 45° C. in order to preserve the active oxygen content of the monomeric reaction participant of the formula as unchanged as possible. In this way copolymers are obtained with an active oxygen content which at higher temperatures are suitable for further reaction while unfolding the initiator activity of the component according to the invention of formula I. The proportion of the compound of formula I as comonomer depends on the desired initiator activity of the intermediate product obtained in this manner. In general 0.5 to 5% of the comonomer of the general formula I is used for the copolymerization. However, for special purposes higher or lower additions may also be used.

The intermediate product obtained in this copolymerization is distinguished above all by a lower sensitivity and thus higher stability than the monomer of the general formula I itself and is therefore particularly suitable for copolymerization with other monomers in particular of styrene, with the base copolymer.

The invention is elucidated further by the following examples.

EXAMPLE 1

Bis-(vinyladipoyl)-peroxide from the acid 0.6 mol (24 g) 85% $H_2O_2$ is added to a solution of 0.8 mol (170 g) dicyclohexylcarbodiimide and 0.04 mol (5 g) 4-dimethylaminopyridine in 200 g toluene while stirring and cooling. A solution of 0.5 mol (87 g) monovinyladipic acid in 100 g toluene is added dropwise at +5° to 10° C. and it is stirred for a further 2 hours at 10° C. The precipitated dicyclohexylurea is removed by filtration, the filtrate is washed twice with 150 ml 10% $Na_2CO_2$ solution and three times with 250 ml 30% $(NH_4)_2SO_4$ solution each time, dried for 30 minutes with 50 g anhydrous $Na_2SO_4$ and filtered.

The solvent is removed in a vacuum on a rotary evaporator at 30° C. bath temperature.

126 g of a viscous liquid is obtained with a content of 73% bis-(vinyladipoyl)-peroxide (VAP; 54% of theory). The product crystallizes in the refrigerator.

EXAMPLE 2

2.1 Production of adipic acid monovinyl ester chloride 1045 g (=6 mol) adipic acid monovinyl ester is melted at 50° C. bath temperature in a 2 l three-necked flask with thermometer, dropping funnel and reflux cooler. 370 g (=2.7 mol) phosphorus trichloride is slowly added dropwise at 50° C. and afterwards allowed to react for a further ca. 2 hours at 50° C. until no further generation of gas occurs.

After cooling to 25° C., the crude acid chloride is decanted from the phosphorous acid. The excess $PCl_3$ is withdrawn in a rotary evaporator in a water-jet vacuum at a bath temperature of 50° C. 1.127 g crude adipic acid monovinyl ester chloride is obtained.

2.2 Bis(vinyladipoyl)-peroxide from the acid chloride 0.6 mol (64 g) sodium carbonate and then 0.33 mol (16 g) 70% hydrogen peroxide are dissolved in a solution of 0.1 mol (4 g) sodium hydroxide in 320 g water. It is cooled to +5° C. while stirring and 0.5 mol (96 g) monovinyladipoyl chloride is then added dropwise within 15–20 minutes at a maximum of 10° C.

It is stirred for a further 15 hours at +5° C. the precipitated solid is then filtered and washed neutral and free of chloride with water in the suction filter.

About 100 g of a moist product with a content of ca. 80% bis-(vinyladipoyl)peroxide is obtained. (90–95% yield).

EXAMPLE 3

Copolymerization with 1% VAP 113 g ethanol was added to a reactor and purged with $N_2$. 0.465 g di-myristylperoxydicarbonate (MYPC) was dissolved in a small amount of vinyl acetate and 69.3 g vinyl acetate and 0.7 g VAP were added. The temperature was adjusted to 40° C. Each hour a sample was taken for monitoring and precipitated in 15% saline solution, washed and dried.

| Time | % conversion of monomers | AO content % | % content of VAP |
|---|---|---|---|
| 3 h | 36% | 0.089% | 1.90% |
| 4 h | 45% | 0.077% | 1.62% |
| 5 h | 65% | 0.068% | 1.45% |
| 6 h | 74% | 0.65% | 1.39% |

EXAMPLE 4

Copolymerization with 3% VAP

The procedure is the same as that in example 3.

| Time | % conversion of monomers | AO content % | % content of VAP |
|---|---|---|---|
| 3½ h | 44% | 0.179% | 3.7% |
| 6 h | 67% | 0.180% | 3.9% |

EXAMPLE 5

Copolymerization with 5% YAP

The procedure is the same as that of example 3.

| Time | % conversion of monomers | AO content % | % content of VAP |
|---|---|---|---|
| 2 h | 25% | 0.54% | 11.5% |
| 3 h | 43% | 0.47% | 10.2% |
| 4 h | 58% | 0.284% | 6.1% |

EXAMPLE 6

Determination of the initiator activity

In order to determine the initiator activity, 50 g styrene was admixed with 0.199 g LP or 0.244 g VAP (70%) and polymerized for 4 h at 90° C. It was dissolved in ca. 80 g toluene and precipitated in ca. 500 ml ethanol and dried at 110° C.

| for LP | conversion 38% |
|---|---|
| for VAP | conversion 44% |

We claim:

1. A diacylperoxide vinyl ester compound of the general formula I

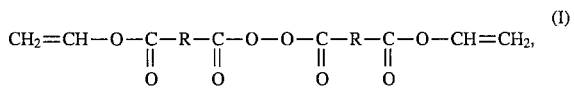

wherein R is an alkylene residue which can be straight-chained, branched or cyclic and contains 2 to 10 C atoms or is an aryl residue.

2. The compound of claim 1 wherein R is a $C_4$–$C_6$ alkylene residue, cyclohexylene or a phenyl residue.

3. The compound of claim 1 wherein R is n-butylene.

4. The compound of claim 1 wherein R is substituted or unsubstituted phenylene.

5. The compound of claim 1 wherein R is cyclohexylene.

6. A process for the production of a compound of claim 1 comprising:

reacting a monovinyldicarboxylic acid of formula II

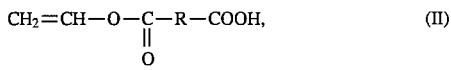 (II)

wherein R is an alkylene residue which can be straight-chained, branched or cyclic and contains 2 to 10 C atoms or is an aryl residue, with at least equimolar amounts of dicyclohexylcarbodiimide and $H_2O_2$ and catalytic amounts of an aromatic amine in an apolar aprotic solvent while cooling.

7. The process of claim 6 wherein the solvent is toluene.

8. The process of claim 6 wherein the catalyst is dimethylaminopyridine.

9. The process of claim 6 wherein the acid of formula II is selected from the group consisting of monovinyladipic acid, monovinylterephthalic acid and monovinylcyclohexyl-1,4-dicarboxylic acid.

10. A process for the production of a compound of claim 1 comprising:

reacting a monovinyldicarboxylic acid chloride of formula III

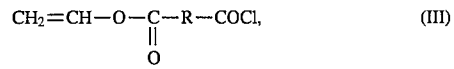 (III)

in which R is an alkylene residue which can be straight-chained, branched or cyclic and contains 2 to 10 C atoms or is an aryl residue, with an alkaline aqueous $H_2O_2$ solution at a temperature of $-10°$ to $+10°$ C.

11. The process of claim 10 wherein the $H_2O_2$ is used in a 20 to 40% excess relative to the acid chloride.

12. The process of claim 10 wherein the acid chloride of formula III is monovinyladipic acid chloride.

13. A copolymerization reaction product of the compound of claim 1 and an olefinic unsaturated monomer.

14. The copolymerization reaction product of claim 13 wherein the olefinic unsaturated monomer is at least one monomer from the group consisting of vinyl acetate, ethylene, styrene, vinyl chloride, methacrylate, methylmethacrylate and vinylidene chloride.

* * * * *